Figure 1:
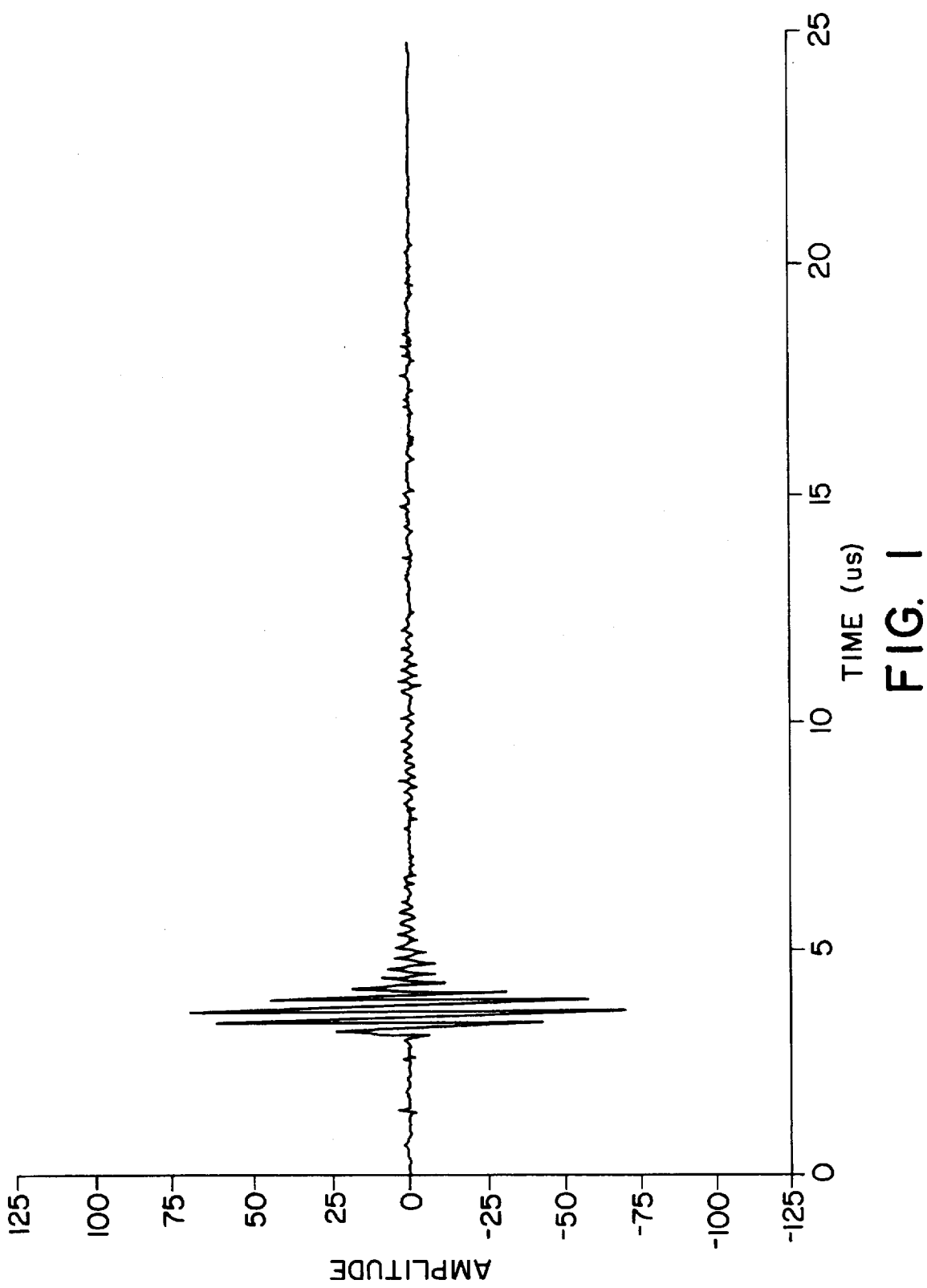

United States Patent [19]
Albayrak et al.

[11] Patent Number: 5,730,954
[45] Date of Patent: Mar. 24, 1998

[54] PREPARATION COMPRISING CAVITATE- OR CLATHRATE-FORMING HOST/GUEST COMPLEXES AS CONTRAST AGENT

[75] Inventors: Celal Albayrak; Georg Rössling; Johannes Tack, all of Berlin, Germany

[73] Assignee: Schering Aktiengesellschaft, Berlin, Germany

[21] Appl. No.: 322,966

[22] Filed: Oct. 13, 1994

Related U.S. Application Data

[63] Continuation of Ser. No. 973,315, Nov. 9, 1992, abandoned, which is a continuation of Ser. No. 656,099, Feb. 25, 1991, abandoned.

[30] Foreign Application Priority Data

Aug. 23, 1988 [DE] Germany ............................ 38 28 905.9

[51] Int. Cl.$^6$ ............................ A61K 49/00; G01N 31/00; G01N 33/48
[52] U.S. Cl. ............................ 424/9.52; 424/9.1; 424/9.5
[58] Field of Search ............................ 424/9, 9.1, 9.5, 424/9.51, 9.52, 400, 450; 128/662.02

[56] References Cited

U.S. PATENT DOCUMENTS

| | | | |
|---|---|---|---|
| 4,276,885 | 7/1981 | Tickner et al. | 128/660 |
| 4,657,756 | 4/1987 | Rasor et al | 424/9 |
| 4,681,119 | 7/1987 | Rasor et al. | 128/662.02 |
| 4,684,479 | 8/1987 | D'Arrigo | 252/307 |
| 4,718,433 | 1/1988 | Feinstein | 128/662.02 |
| 4,844,882 | 7/1989 | Widder et al. | 424/9 |
| 4,925,652 | 5/1990 | Gries et al. | 424/9 |

FOREIGN PATENT DOCUMENTS 36 37 926  11/1987  Germany.

OTHER PUBLICATIONS

Barrer, RM et al. Chem. Abs. 85(8):52089K (1976) From: J. Chem. Soc. Chem. Commun, 9:333–4 (1976).
Mock et al., Industrial and Engineering Chemistry, vol. 53, No. 12, p. 1007 (1961), on p–hydrochinon.
Allison et al., Trans. Faraday Soc. 64, p. 549 (1968) on quinol.
Allison et al., Trans. Faraday Soc. 64, p. 549 (1968) on phenol.
Sixou et al., Berichte der Bunsen–Gesellschaft, Bd. 80, No. 5, p. 364 (1976) on quinol.
Sixou et al., Berichte der Bunsen–Gesellschaft, Bd. 80, No. 5, p. 364 (1976) on water.
Brown et al., J. Amer. Chem. Soc. 105, pp. 4561–4571 (1983) on thiourea.
Arad–Yellin et al., J. Amer. Chem. Soc. 105, pp. 4561–4571 (1983) on tri–o–thymotide.
Gilmore et al., J. Chem. Soc., Perkin II, p. 1427 (1977) on 2–phenyl–3–p(2,2, 4–trimethylchroman–4–yl)phenylquinazolin–4(3H)–one.
Baker et al., J. Chem. Soc., p. 2010 (1956) on dianin.
Barrer et al., J. Chem. Soc. p. 333 (1976) on dianin.
Mandelcorn et al., J. Chem. Soc. 82, p. 3297 (1960) on dianin.
MacNicol, Chemical Communications, p. 836 (1969) on dianin.
Cramer, Angewandte Chemie 64, Nr. 16, pp. 437–447 (1952).
Bouchard et al., Clathration, vol. 6, pp. 179–189 (1977).
Frank, "Inclusion Compounds," Journal of Pharmaceutical Sciences, vol. 64, No. 10, Oct. 1975, 3 pp.
McNichol et al., "Clathrates and Molecular Inclusion Phenomena," Silicon in Organic Synthesis, pp. 65–67 (1978).
MacNicol, "Structure and Design of Inclusion Compounds: The Clathrates of Hydroquinone, Phenol . . . " Academic Press, London (1984), pp. 1–45.
Makin, Clathration, Kirk–Othmer, vol. 6, pp. 179–189 (1980).
Carroll et al., "Gelatin Encapsulated Nitrogen Microbubbles as Ultrasonic Contrast Agents," *Investigative Radiology*, vol. 15, No. 3, pp. 260–266, May–Jun. 1980.
Patent Abstracts of Japan, vol. 5, No. 160 (C–75) [832], Oct. 15, 1981 (Abstract of JP–A–56 92 221).

*Primary Examiner*—John Kight
*Assistant Examiner*—Dameron Jones
*Attorney, Agent, or Firm*—Millen, White, Zelano & Branigan, P.C.

[57] ABSTRACT

A method of using cavitate- or clathrate-forming host/guest complexes for the preparation of contrast media in ultrasonic examination is provided. The host/guest complexes have a host which dissolves in a liquid carrier, releasing the guest (inert gas). With such contrast media, it is possible to diagnose blood and its flow conditions in the heart, and other organs, such as the myocardium, liver, spleen, and kidneys. Other internal systems such as the urinary ducts, the gastrointestinal tract, joints, and eyes can also be imaged.

15 Claims, 4 Drawing Sheets

PREPARATION COMPRISING CAVITATE- OR CLATHRATE-FORMING HOST/GUEST COMPLEXES AS CONTRAST AGENT

This application is a continuation of application Ser. No. 07/973,315, filed Nov. 9, 1992, now abandoned, which is a continuation of application Ser. No. 07/656,099, filed Feb. 25, 1991, now abandoned.

The invention relates to a preparation comprising cavitate- or clathrate-forming host/guest complexes, the host molecules of which are dissolved in a liquid vehicle with release of the guest, for use as contrast media in ultrasonic, x-ray, or NMR examination.

The manufacture of stoichiometric host/guest complexes comprising host molecules, significantly organic onium compounds and gases or gas formers as guest molecules has already been described in literature (Angew. Chem. 97 (1985) 721). Use of the host/guest complexes as contrast agents has not been described.

The invention is based on the problem of providing for ultrasonic, X-ray or NMR investigations a preparation which can be used as a transport medium for contrast agents. In particular the invention is to provide host/guest complexes which store the largest possible guest volume in a minimal host mass.

It has surprisingly been found that the cavitates or clathrates, which form host/guest complexes where the host molecules dissolve in a liquid vehicle with release of the guest, form a transport medium which can completely decompose and can thus be chosen so that they do not exert any toxic influence on the biological substance in which the investigation is to be carried out.

The preparation used for ultrasonic investigation can advantageously contain as host molecules water, urea and derivatives thereof, thiourea and derivatives thereof, phenol and substituted phenols, dihydroxybenzenes and derivatives thereof, hydroquinone and substituted hydroquinones, salicyclic acid and derivatives thereof, tri-o-thymotide and derivatives thereof, ascorbic acid, flavins and derivatives thereof, flavanols and derivatives thereof, cyclophanes and derivatives thereof, guaiacamine, naphthohydroquinone and derivatives thereof, cyclodextrin and derivatives thereof, in particular dimethyl-1-cyclodextrin, methyl-β-cyclodextrin, hydroxypropyl-β-cyclodextrin, chromanes and derivatives thereof, in particular 4-p-hydroxyphenyl-2,2,4-trimethylchromane, 4-p-hydroxyphenyl-2,2,4-trimethylthiochromane, 4-p-hydrophenyl-2,2,4,7-tetramethylthiochromane; 4-p-hydroxyphenyl-2,2,4-trimethylselenium chromane, hexahost compounds, in particular hexakis(phenylthio)benzene and derivative thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetra-salicylides, 9,9'-spirobifluorene-2,2'-dicarboxylacid, choleic acids, 4-4'dinitrodiphenyl, bis-(N,N'-alkylene-benzidine), bis-(N,N'-tetramethylenebenzidine), desoxycholic acid, monoaminonickel (II)-cyanide, tetra(4-methyl-pyridine)-nickel (II)-dithiocyanates and derivatives thereof, hexamethylisocyanidoferronchloride, 2-phenyl-3-p(2,2,4-trimethyl chroman-4-yl)-phenylquinazoline-4, cyclotriphosphazones, tris-1,2-phenyldioxycyclotriphosphazones and as guest molecules: inert gases and inert gas compounds, sulphur halides, nitrogen and nitrogen oxides, carbon oxides, hydrogen and hydrogen oxides, sulphur oxides, hydrogen phosphides, hydrogen halides, uranium halides and oxygen as well as hydrocarbons and derivatives thereof, epoxides, ether and halogenated hydrocarbons The preparation used for ultrasonic investigations can especially advantageously contain as guest molecules helium, neon, argon, krypton, xenon, radon, sulphur hexafluoride, water, hydrogen peroxide, nitrogen monoxide, carbon monoxide, carbon dioxide, hydrogen iodide, xenon difluoride, xenon tetrafluoride, xenonhexafluoride, xenon dioxide, sulphur dioxide, sulphur trioxide, arsenic hydride, hydrogen phosphide, deuterium, uranium hexafluoride, methane, ethane, propane, cyclopropane, butane, pentane, ethylene oxide and methyl bromide.

The crystalline complexes can be influenced in their particle size in particular by the crystallisation conditions and also by the mechanical processes of the particle breakdown (air jet grinding).

The crystalline complexes can be coated with hydrophilic, lipophilic or amphiphilic auxiliary products.

Suitable vehicles for applying the complexes are sterile aqueous systems with additives to adjust the viscosity, surface tension, pH-value and osmotic pressure wherein the complexes are dissolved, or suspended and optionally emulsified preferably prior to use.

The host/guest complexes are introduced into an aqueous vehicle. As the host molecules dissolve the complexes are broken down through the release of the gas bubbles into the vehicle.

The host molecules dissolved in the vehicle no longer have any complexing properties. The speed of the gas release, and the size and duration of the gas bubbles can be adjusted within a wide range through the type of gas or gas-former enclosed, through the type of host molecule and by the surface or particle size in dependence on the viscosity, surface tension of the vehicle.

It is thus surprisingly possible to obtain in a very simple way injectable, gas-containing pharmaceutical preparations with excellent echogenic properties.

In particular it is possible to prepare the gas volume of about 150 µl required for in vivo contrasting eg of the left ventricle of a human being through very low amounts of active ingredient in the range from 2–10 mg/appln., as shown by the following composition:

| Hydroqinone/$N_2$ | 3:1 Complex | 1 mg | 70 µl |
|---|---|---|---|
| Hydroqinone/Xe | 3:1 Complex | 1 mg | 53 µl |
| Dianin/$SF_6$ | 3:1 Complex | 1 mg | 26 µl |
| Dianin/Argon | 2:1 Complex | 1 mg | 26 µl |
| Tri-o-thymotide/methane | 2:1 Complex | 1 mg | 23 µl |
| Tri-o-thymotide $CH_3Br$ | 2:1 Complex | 1 mg | 21 µl |
| Dianin/N2 | | 1 mg | 103 µl |

4-(4-hydroxyphenyl)-2,2,4-trimethyl-chromane) is named as the dianin compound and produced according to J. Russ Phys. Chem. Soc. 46,1310 (1914) and Chem. Zentr. 1915,I,1063.

It is thus possible to prepare a contrast agent for ultrasonic diagnostics which after intravenous application is able to show up the blood and its flow conditions in the right side of the heart and after passing through the pulmonary capillary bed on the left side for ultrasound. Furthermore it also is to show the circulation to other organs, such as the myocardium, liver, spleen and kidneys. It can similarly be used to show the urinary ducts, gastro-intestinal tract, joints, frontal sinus and eyes.

Particularly when using gas molecules (eg xenon) which are able to overcome the blood/brain barrier, it is also possible to show the cerebrum and its physiological and pathological structures through ultrasound.

If the preparation according to the invention also contains eg xenon then it is possible to use this host/guest complex as an X-ray contrast agent. When using stable radicals (eg oxygen-, nitroxyl-) the preparations according to the invention can also be used as NMR-contrast agents.

The invention will now be explained by the following examples.

1. Tri-o-thymotide/methyl bromide

Tri-o-thymotide (25 g) was dissolved in 2,2,4-trimethylpentane (50 ml) at 100° C. and the hot solution was introduced into the high pressure autoclave. Methyl bromide was added to the autoclave until a pressure of 200 bar was reached. The high pressure autoclave was then kept for 2 hours at 110° C. and the solution was then cooled down to room temperature within 5 days. The crystals were filtered off and washed 3 times with cold 2,2,4-trimethylpentane. The crystals were then dried in the drying cabinet at 50° C.

2. Dianin-compound (4-p-hydroxyphenyl-2,2,4-trimethylchroman)/ethylene oxide

Dianin compound (25 g) was dissolved in 1-decanol (35 g) at 125° C. The hot solution was introduced into the high pressure autoclave. The solution was subjected to compressed ethylene oxide of 300 bar. The high pressure autoclave was kept for 2 hours at 140° C. and the solution then cooled down to room temperature within 8 days. The crystals were filtered off and washed 4 times with cold 1-decanol (5 ml). The crystals were then dried in the drying cabinet at 100° C.

3. Dianin-compound (4-p-hydroxyphenyl-2,2,4-trimethylchroman/sulphur hexafluoride Dianin compound (25 g) was dissolved in 1-decanol (35 g) at 125° C. The hot solution was introduced into the high pressure autoclave. The solution was subjected to compressed sulphur hexafluoride of 300 bar. The high pressure autoclave was tempered for 2 hours at 140° C. The solution was then cooled down to room temperature within 8 days. The crystals were filtered off and washed 4 times with cold 1-decanol (5 ml). The crystals were subsequently dried in the drying cabinet at 100° C.

4. Dianin-compound (4-p-hydroxyphenyl-2,2,4-trimethylchroman)/ethane

Dianin-compound (25 g) was dissolved in 1-decanol (35 g) at 125° C. The hot solution was introduced into the high pressure autoclave. The solution was subjected to compressed ethane of 300 bar. The high pressure autoclave was kept for 2 h at 140° C. The solution was then cooled down to room temperature within 8 days. The crystals were filtered off and washed 4 times with cold 1-decanol (5 ml). Then the crystals were dried in the drying cabinet at 100° C.

5. Dianin-compound (4-p-hydroxyphenyl-2,2,4-trimethylchroman)/propane

Dianin compound (25 g) was dissolved in 1-decanol (35 g) at 125° C. The hot solution was introduced into the high pressure autoclave. The solution was subjected to compressed propane of 300 bar. The high pressure autoclave was kept for 2 h at 140° C. The solution was then cooled down to room temperature within 8 days. The crystals were filtered off and washed 4 times with cold 1-decanol (5 ml). The crystals were then dried in the drying cabinet at 100° C.

6. Dianin-compound (4-p-hydroxyphenyl-2,2,4-trimethylchroman)/carbon dioxide

Dianin-compound (25 g) was dissolved in 1-decanol (35 g) at 125° C. The hot solution was introduced into the high pressure autoclave. The solution was subjected to compressed carbon dioxide of 300 bar. The high pressure autoclave was kept for 2 h at 140° C. The solution was then cooled down to room temperature within 8 days. The crystals were filtered off and washed 4 times with cold 1-decanol (5 ml). The crystals were then dried in the drying cabinet at 100° C.

7. Dianin-compound (4-p-hydroxyphenyl-2,2,4-trimethylchroman/cyclopropane

Dianin-compound (25 g) was dissolved in 1-decanol (35 g) at 125° C. The hot solution was introduced into the high pressure autoclave. The solution was subjected to compressed cyclopropane of 300 bar. The high-pressure autoclave was kept for 2 h at 140° C. The solution was then cooled down to room temperature within 8 days. The crystals were filtered off and washed 4 times with cold 1-decanol (5 ml). The crystals were dried in the drying-cabinet at 100° C.

8. Dianin-compound (4-p-hydroxyphenyl-2,2,4-trimethylchroman)/methane

Dianin-compound (25 g) was dissolved in 1-decanol (35 g) at 125° C. The hot solution was introduced into the high pressure autoclave. The solution was subjected to compressed methane of 300 bar. The high pressure autoclave was kept for 2 h at 140° C. The solution was then cooled down to room temperature within 8 days. The crystals were filtered off and washed 4 times with cold 1-decanol (5 ml). The crystals were dried in the drying cabinet at 100° C.

9. Dianin-compound (4-p-hydroxyphenyl-2,2,4-trimethylchroman)/nitrogen

Dianin-compound (25 g) was dissolved in 1-decanol (35 g) at 125° C. The hot solution was introduced into the high pressure autoclave. The solution was subjected to compressed nitrogen of 300 bar. The high pressure autoclave was kept for 2 h at 140° C. The solution was then cooled down to room temperature within 8 days. The crystals were filtered off and washed 4 times with cold 1-decanol (5 ml). The crystals were then dried in the drying cabinet at 100° C.

Melting point: 162.88° C.

10. Dianin-compound (4-p-hydroxyphenyl-2,2,4-trimethylchroman)/xenon

Dianin-compound (25 g) was dissolved in 1-decanol (35 g) at 125° C. The hot solution was introduced into the high pressure autoclave. The solution was subjected to compressed xenon of 300 bar. The high pressure autoclave was kept for 2 h at 140° C. The solution was then cooled down to room temperature within 8 days. The crystals were filtered off and washed 4 times with cold 1-decanol (5 ml). The crystals were then dried in the drying cabinet at 100° C.

11. Dianin-compound (4-p-hydroxyphenyl-2,2,4-trimethylchroman)/argon

Dianin-compound (25 g) was dissolved in 1-decanol (35 g) at 125° C. The hot solution was introduced into the high pressure autoclave. The solution was subjected to compressed argon of 300 bar. The high pressure autoclave was kept for 2 h at 140° C. The solution was then cooled down to room temperature within 8 days. The crystals were filtered off and washed 4 times with cold 1-decanol (5 ml). The crystals were then dried in the drying cabinet at 100° C.

Melting point: 160.84° C.

12. Hydroquinone/methane

Hydroquinone (30 g) was dissolved in n-propanol (70 ml) at 70° C. The hot solution was introduced into the high pressure autoclave. The solution was subjected to compressed methane of 300 bar. The high pressure autoclave was kept for 2 h at 80° C. The solution was then cooled down to room temperature within 5 days. The crystals were filtered off and then washed 4 times with cold n-propanol (5 ml). The crystals were dried in the drying cabinet at 70° C. subsequently.

13. Hydroquinone/sulphur hexafluoride

Hydroquinone (30 g) was dissolved in n-propanol (70 ml) at 70° C. The hot solution was introduced into the high pressure autoclave. The solution was subjected to compressed sulphur hexafluoride of 300 bar. The high pressure autoclave was kept for 2 h at 80° C. The solution was then cooled down to room temperature within 5 days. The crystals were filtered off and washed 4 times with cold n-propanol (5 ml). The crystals were then dried in the drying cabinet at 70° C.

14. Hydroquinone/propane

Hydroquinone (30 g) was dissolved in n-propanol (70 ml at 70° C. The hot solution was introduced into the high pressure autoclave. The solution was subjected to compressed propane of 300 bar. The high pressure autoclave was kept for 2 h at 80° C. The solution was then cooled down to room temperature within 5 days. The crystals were filtered off and washed 4 times with cold n-propanol ( 5 ml). The crystals were then dried in the drying cabinet at 70° C.

15. Hydroquinone/ethane

Hydroquinone (30 g) was dissolved in n-propanol (70 ml) at 70° C. The hot solution was introduced into the high pressure autoclave. The solution was subjected to compressed ethane of 300 bar. The high pressure autoclave was kept for 2 h at 80° C. The solution was then cooled down to room temperature within 5 days. The crystals were filtered off and washed 4 times with cold n-propanol (5 ml). Then the crystals were dried in the drying cabinet at 70° C.

16. Hydroquinone/carbon dioxide

Hydroquinone (30 g) was dissolved in n-propanol (70 ml) at 70° C. The hot solution was introduced into the high pressure autoclave. The solution was subjected to compressed carbon dioxide of 300 bar. The high pressure autoclave was kept for 2 h at 80° C. Then the solution was cooled down to room temperature within 5 days. The crystals were filtered off and washed 4 times with cold n-propanol (5 ml). The crystals were then dried in the drying cabinet at 70° C.

17. Hydroquinone/ethylene oxide

Hydroquinone (30 g) was dissolved in n-propanol (70 ml) at 70° C. The hot solution was introduced into the high pressure autoclave. The solution was subjected to compressed ethylene oxide of 300 bar. The high pressure autoclave was kept for 2 h at 80° C. The solution was then cooled down to room temperature within 5 days. The crystals were filtered off and washed 4 times with cold n-propanol (5 ml). The crystals were then dried in the drying cabinet at 70° C.

18. Hydroquinone/cyclopropane

Hydroquinone (30 g) was dissolved in n-propanol (70 ml) at 70° C. The hot solution was introduced into the high pressure autoclave. The solution was subjected to compressed cyclopropane of 300 bar. The high pressure autoclave was kept for 2 h at 80° C. The solution was then cooled down to room temperature within 5 days. The crystals were filtered off and washed 4 times with cold n-propanol (5 ml). The crystals were then dried in the drying cabinet at 70° C.

19. Hydroquinone/nitrogen

Hydroquinone (30 g) was dissolved in n-propanol (70 ml) at 70° C. The hot solution was introduced into the high pressure autoclave. The solution was subjected to compressed nitrogen of 300 bar. The high pressure autoclave was kept for 2 h at 80° C. The solution was then cooled down to room temperature within 5 days. The crystals were filtered off and washed 4 times with cold n-propanol (5 ml). The crystals were dried in the drying cabinet thereafter at 70° C.

Melting point: 176.92° C.

20. Hydroquinone/xenon

Hydroquinone (30 g) was dissolved in n-propanol (70 ml) at 70° C. The hot solution was introduced into the high pressure autoclave. The solution was subjected to compressed xenon of 300 bar. The high pressure autoclave was kept for 2 h at 80° C. The solution was then cooled down to room temperature within 5 days. The crystals were filtered off and washed 4 times with cold n-propanol (5 ml). The crystals were then dried in the drying cabinet at 70° C.

21. Hydroquinone/argon

Hydroquinone (30 g) was dissolved in n-propanol (70 ml) at 70° C. The hot solution was placed in the high pressure autoclave. The solution was subjected to compressed argon of 300 bar. The high pressure autoclave was kept at 80° C. for 2 h. The solution was then cooled down to room temperature within 5 days. The crystals were filtered off and washed 4 times with cold n-propanol (5 ml). The crystals were then dried in the drying cabinet at 70° C.

Melting point: 175.67° C.

22. Urea/butane 4 g urea were dissolved in 12 ml ethanol at 60° C. The solution was then placed in an high pressure autoclave and subjected to a butane pressure of 150 bar. The solution was cooled down from 60° C. to room temperature within 48 h. The solution with h/g crystals was removed from the autoclave, filtered and the h/g crystals were washed with 10 ml cold ethanol. The h/g complex crystals were dried in the vacuum cabinet at 60° C.

23. Urea/isobutane 4 g urea were dissolved in 12 ml ethanol at 60° C. The solution was then placed in a high pressure autoclave and subjected to an isobutane pressure of 150 bar. The solution was cooled down from 60° C. to room temperature within 48 h. The solution with h/g crystals was removed from the autoclave, filtered and the h/g crystals were washed with 10 ml cold ethanol. The h/g complex cystals were dried in the vacuum cabinet at 60° C.

Melting point: 138.50 ° C.

24. Urea/neopentane 4 g urea were dissolved in 12 ml ethanol at 60° C. The solution was then placed in a high pressure autoclave and subjected to a neopentane pressure of 150 bar. The solution was cooled down from 60° C. to room temperature within 48 h. The solution with h/g crystals was removed from the autoclave, filtered and the h/g crystals were washed with 10 ml cold ethanol. The h/g complex crystals were dried in the vacuum cabinet at 60° C.

Melting point: 138.79° C.

25. Thiourea/butane 4 g thiourea were dissolved in 12 ml ethanol at 60° C. The solution was then placed in a high pressure autoclave and subjected to a butane pressure of 150 bar. The solution was cooled down to room temperature within 60 h. The solution with h/g crystals was removed from the autoclave, filtered and the h/g crystals were washed with 10 ml cold ethanol. The h/g complex crystals were dried in the vacuum cabinet at 60° C.

26. Thiourea/isobutane 4 g thio urea were dissolved in 20 ml ethanol at 600° C. The solution was then placed in a high pressure autoclave and subjected to an isobutane pressure of 150 bar. The solution was cooled down to room temperature within 60 h. The solution with h/g crystals was removed from the autoclave, filtered and the h/g crystals were washed with 10 ml cold ethanol. The h/g complex crystals were dried in the vacuum cabinet at 60° C.

Melting point: 181.34° C.

27. Thiourea/neopentane 4 g thiourea were dissolved in 20 ml ethanol at 60° C. The solution was then placed in a high pressure autoclave and subjected to a neopentane pressure of 150 bar. The solution was cooled down to room temperature within 60 h. The solution with h/g crystals was removed from the autoclave, filtered and the h/g crystals were washed with 10 ml cold ethanol. The h/g complex crystals were dried in the vacuum cabinet at 60° C.

28. Vehicle

A: The following solutions for example are suitable as a vehicle for hydroquinone-, tri-O-thymotide-urea- and thiourea-h/g complexes:
a) 1% gelatine solution
b) 1% albumin solution
c) 10 % glycerin solution
d) 15 % propylene glycol solution
e) Mixtures of sodium cholate and phosphatidylcholine in water
f) 0.01–1% phosphatidylcholine dispersion (aqueous)
g) 1% methyl cellulose
h) 1–2% dextran solution
i) 1% agar solution
j) 2% Tween solution (Tween 80)
k) 1% gum arabic B: The following vehicles are suitable for dianin-h/g-complexes, for example:
a) 10–20% 2-(2-methoxyethoxy)-ethanol
b) Mixtures of 2-(2 methoxyethoxy)-ethanol (20 %) and Tween 80 (1%)

In vitro ultrasonic investigations

The acoustic properties of the h/g complex-vehicle systems were determined with in-vitro ultrasonic investigations.

For this about 1–5 mg of the h/g complexes were mixed in 10–20 ml with one of the said vehicles and then examined with ultrasonic scanners.

The ultrasonic scanner Ekoline 20A/S was used in the frequency range 1–5 MHz for qualitative examinations.

Quantitative measurements of the acoustic properties were obtained in an apparatus with the ultrasonic scanner Kraut-Kraemer U.S.I. P-12 at 4 MHz. The results of four systems are detailed here by way of example (FIGS. 1–4).

FIG. 1: Urea/isobutane (Example 23) in 2% Tween 80 solution

Figure 2:
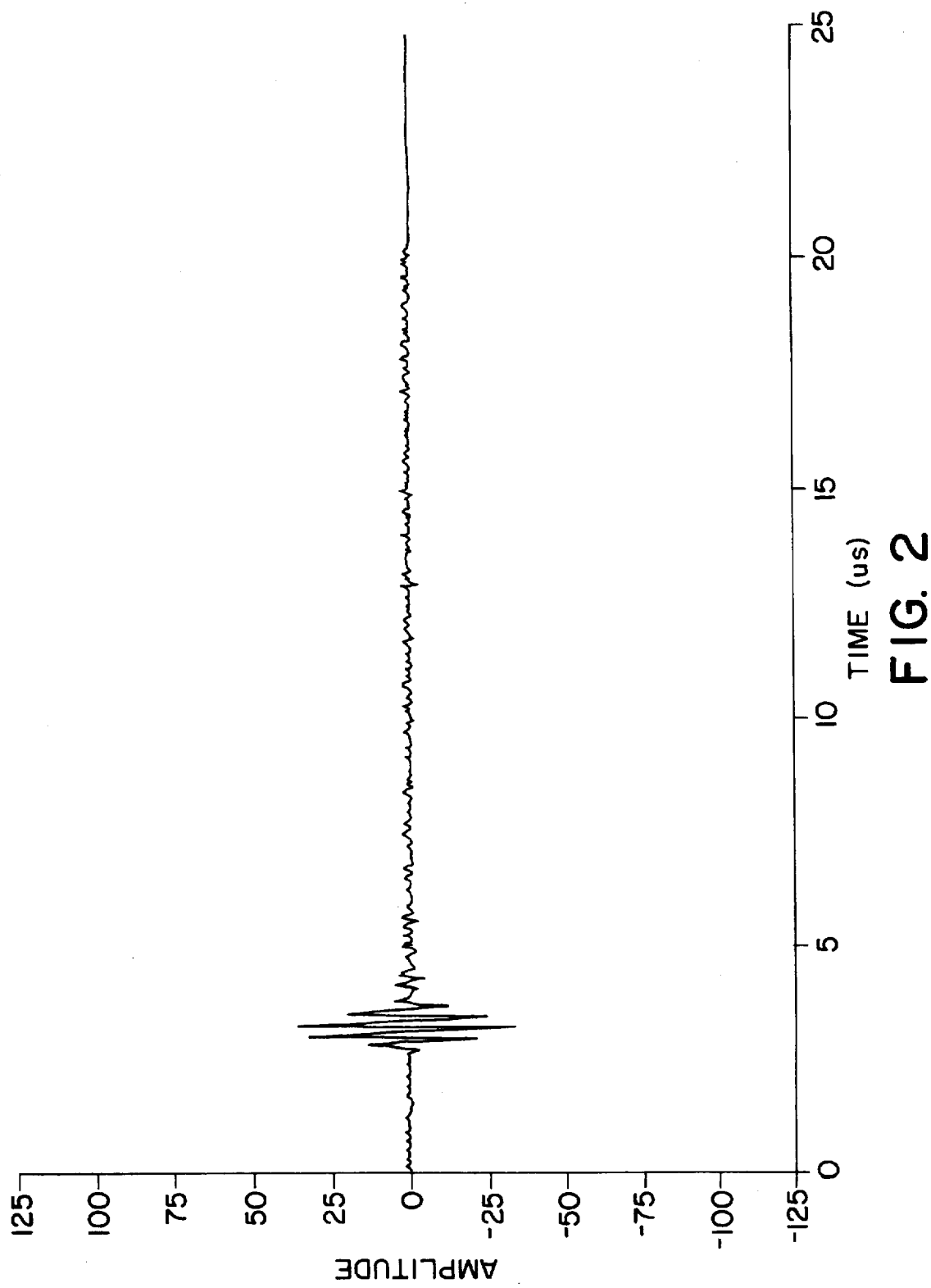

FIG. 2: Thiourea/isobutane (Example 26) in 1% dextran solution

Figure 3:
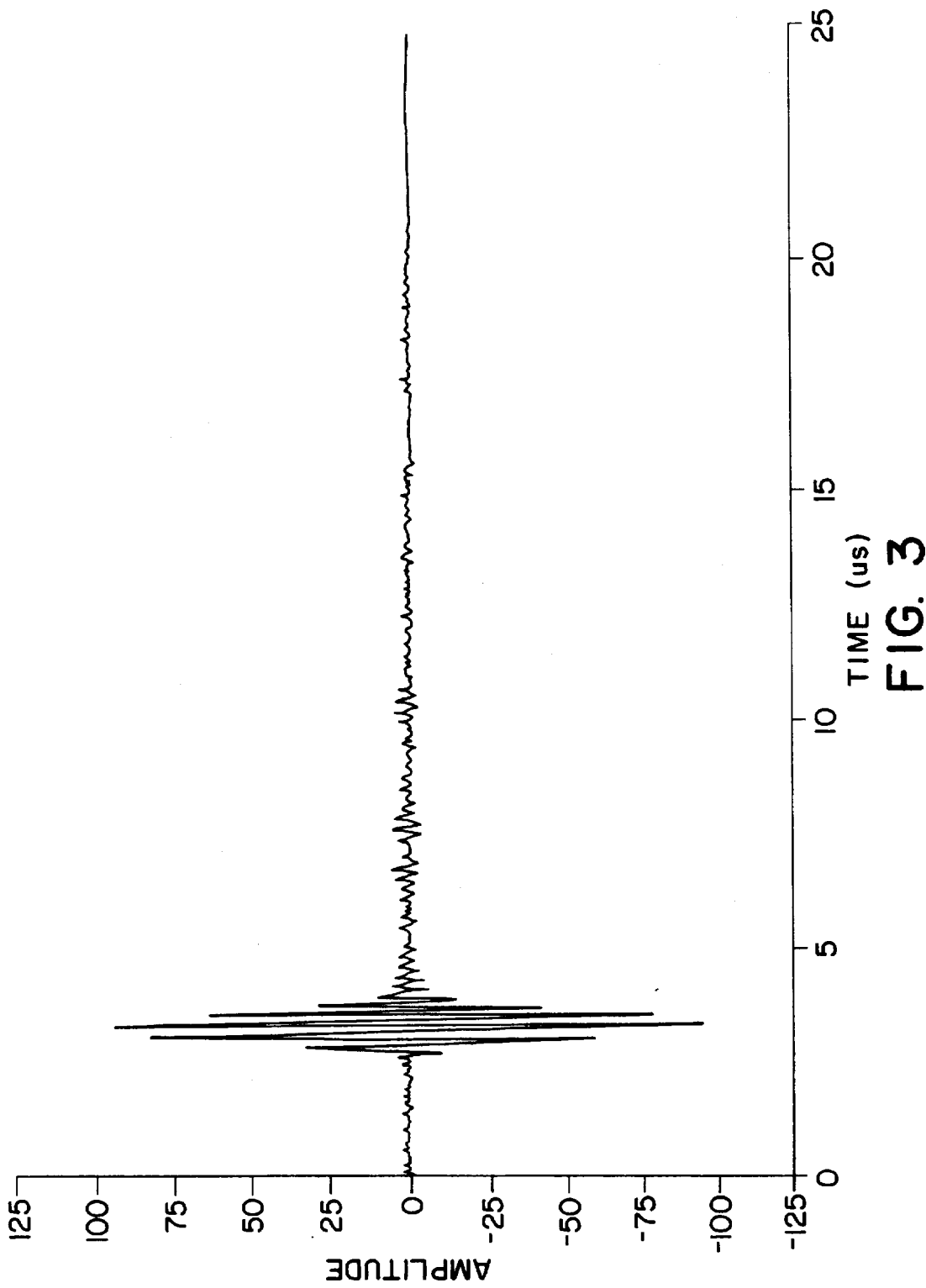

FIG. 3: Hydroquinone/argon (Example 21) in 1% gelatine solution

Figure 4:
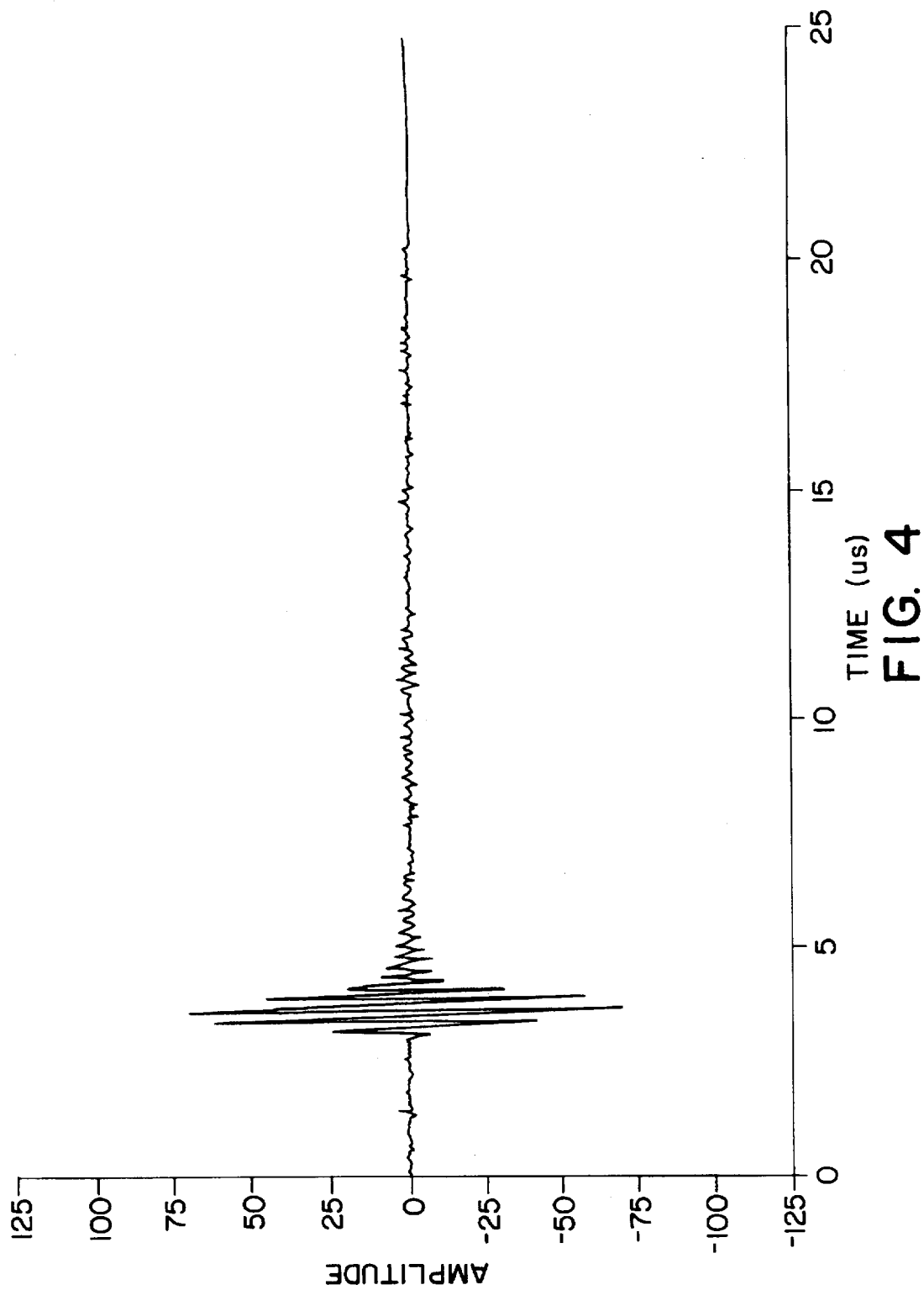

FIG. 4: Dianin/argon (Example 11) in 10% 2 (2-methoxyethoxy)ethanol

To explain the ultrasonic measuring apparatus and the diagrams obtained therefrom:

The apparatus comprises an ultrasonic transmitter combined with a receiver and measuring bulb which contains the specimen. An ultrasonic impulse is transmitted to measure the acoustic properties of the specimen. Reflected ultrasound is measured by the receiver and indicated through a change in the amplitude (see diagram). The diagrams each only show one amplitude change which results from the reflection of the ultrasound from the front wall of the measuring bulb. A second amplitude change which results from reflection from the back wall of the measuring bulb is only obtained with non-echogenic substances (eg water). In the case of echogenic substances a second reflected signal is not obtained since the ultrasound is dissipated in the specimen or changed so that it can no longer be received.

We claim:

1. A method of performing ultrasonic imaging within an animal or specimen, comprising administering to said host or specimen in an amount effective to enhance ultrasonic contrast, cavitate- or clathrate-forming host/guest (H/G) complexes, the host molecules of which are dissolved in a liquid vehicle with release of the guest, wherein the host molecules are selected from the group consisting of:

urea and derivatives thereof, thiourea and derivatives thereof, phenol and substituted phenols, dihydroxybenzenes and derivatives thereof, hydroquinone and substituted hydroquinones, salicylic acid and derivatives thereof, tri-o-thymotide and derivatives thereof, ascorbic acid, flavins and derivatives thereof, flavanols and derivatives thereof, cyclophane and derivatives thereof, guaiacamine, naphthohydroquinones and derivatives thereof, chromanes and derivatives thereof, including 4-p-hydroxyphenyl-2,2,4-trimethylchroman, 4-p-hydroxyphenyl-2,2,4-trimethylthiochroman, 4-p-hydroxyphenyl-2,2,4,7-tetramethylthiochroman, 4-p-hydroxyphenyl-2,2,4-trimethylseleniumchroman, hexahost compounds, including hexakis(phenylthio) benzene and derivatives thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetrasalicylides, 9,9'-spirobifluorene-2,2'-dicarboxyl acid, choleic acids, 4,4'-dinitrodiphenyl, bis (N,N'-alkylene-benzidine), bis(N,N'-tetramethylenebenzidine), desoxycholic acid, tetra-(4-methylpyridine)nickel(II)-dithiocyanates and derivatives thereof, hexamethylisocyanidoferronchlorides, 2-phenyl-3-p-(2,2,4-trimethylchroman-4-yl)phenylquinazolin-4, cyclotriphosphazone, and tris-1,2-phenyldioxycyclotriphosphazones, and guest molecules selected from the group consisting of:

inert gases and inert gas compounds, sulfur halides, nitrogen and nitrogen oxides, carbon oxides, hydrogen and hydrogen oxides, sulfur oxides, hydrogen halides and oxygen, as well as hydrocarbons and derivatives thereof, epoxides, ethers and halogenated hydrocarbons.

2. A method as in claim 1, wherein the cavitate- or clathrate-forming host/guest complexes contain as guest molecules:

helium, neon, argon, krypton, xenon, radon, sulfur hexafluoride, water, hydrogen peroxide, nitrogen monoxide, carbon monoxide, carbon dioxide, hydrogen iodide, xenon difluoride, xenon tetrafluoride, xenon hexafluoride, xenon dioxide, sulfur dioxide, sulfur trioxide, arsenic hydride, hydrogen phosphide, deuterium, uranium hexafluoride, methane, ethane, propane, cyclopropane, butane, pentane, ethylene oxide, and methyl bromide.

3. A method of enhancing an ultrasonic image of a liquid which comprises administering an effective amount of an ultrasonic contrast agent comprising cavitate- or clathrate-forming host/guest (H/G) complexes, the host molecules of which dissolve in a liquid vehicle with release of the guest, and taking an ultrasonic image of said liquid wherein the host molecules are selected from the group consisting of:

urea and derivatives thereof, thiourea and derivatives thereof, phenol and substituted phenols, dihydroxybenzenes and derivatives thereof, hydroquinone and substituted hydroquinones, salicylic acid and derivatives thereof, tri-O-thymotide and derivatives thereof, ascorbic acid, flavins and derivatives thereof, flavanols and derivatives thereof, cyclophane and derivatives thereof, guaiacamine, naphthohydroquinones and derivatives thereof, chromanes and derivatives thereof, including 4-o-hydroxyphenyl-2,2,4-trimethylchroman, 4-p-hydroxyphenyl-2,2,4-trimethylthiochroman, 4-p-hydroxyphenyl-2,2,4,7-tetramethylthiochroman, 4-p-hydroxyphenyl-2,2,4-trimethylseleniumchroman, hexahost compounds, including hexakis(phenylthio) benzene and derivatives thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetrasalicylides, 9,9'-spirobifluorene-2,2'-dicarboxyl acid, choleic acids, 4,4'-dinitrodiphenyl, bis (N,N'-alkylene-benzidine), bis(N,N'-tetramethylenebenzidine), desoxycholic acid, tetra-(4-methylpyridine)nickel(II)-dithiocyanates and derivatives thereof, hexamethylisocyanidoferronchlorides, 2-phenyl-3-o-(2,2,4-trimethylchroman-4-yl)phenylquinazoline-4, cyclotriphosphazone, and tris-1,2-phenyldioxycyclotriphosphazones, and guest molecules selected from the group consisting of:

inert gases and inert gas compounds, sulfur halides, nitrogen and nitrogen oxides, carbon oxides, hydrogen and hydrogen oxides, sulfur oxides, hydrogen halides and oxygen, as well as hydrocarbons and derivatives thereof, epoxides, ethers and halogenated hydrocarbons.

4. A method of enhancing an ultrasonic image of a patient which comprises administering to a patient an effective amount of an ultrasonic contrast agent comprising cavitate- or clathrate-forming host/guest (H/G) complexes, the host molecules of which are dissolved in a liquid vehicle with release of the guest, and taking an ultrasonic image of said patient wherein the host molecules are selected from the group consisting of:

urea and derivatives thereof, thiourea and derivatives thereof, phenol and substituted phenols, dihydroxybenzenes and derivatives thereof, hydroquinone and substituted hydroquinones, salicylic acid and derivatives thereof, tri-o-thymotide and derivatives thereof, ascorbic acid, flavins and derivatives thereof, flavanols and derivatives thereof, cyclophane and derivatives thereof, guaiacamine, naphthohydroquinones and derivatives thereof, chromanes and derivatives thereof, including 4-o-hydroxyphenyl-2,2,4-trimethylchroman, 4-p-hydroxyphenyl-2,2,4-trimethyltriochroman, 4-p-hydroxyphenyl-2,2,4,7-tetramethylthiochroman, 4-p-hydroxyphenyl-2,2,4-trimethylseleniumchroman, hexahost compounds, including hexakis(phenylthio) benzene and derivatives thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetrasalicylides, 9,9'-spirobifluorene-2,2'-dicarboxyl acid, choleic acids, 4,4'-dinitrodiphenyl, bis (N,N'-alkylene-benzidine), bis(N,N'-tetramethylenebenzidine), desoxycholic acid, tetra-(4-methylpyridine)nickel(II)-dithiocyanates and derivatives thereof, hexamethylisocyanidoferronchlorides, 2-phenyl-3-p-(2,2,4-trimethylchroman-4-yl)phenylquinazoline-4, cyclotriphosphazone, and tris-1,2-phenyldioxycyclotriphosphazones, and guest molecules are selected from the group consisting of:

inert gases and inert gas compounds, sulfur halides, nitrogen and nitrogen oxides, carbon oxides, hydrogen and hydrogen oxides, sulfur oxides, hydrogen halides and oxygen, as well as hydrocarbons and derivatives thereof, epoxides, ethers and halogenated hydrocarbons.

5. A method for enhancing the contrast of a cardiac ultrasonic image which comprises injecting an effective amount of an ultrasonic contrast agent comprising cavitate and clathrate forming host/guest (H/G) complexes, the host molecule of which are dissolved in a liquid vehicle with release of the guest, into the bloodstream of a patient and obtaining an ultrasonic image of the heart, the cavitate- or clathrate-forming host/guest complexes of said ultrasonic contrast agent comprising:

host molecules selected from the group consisting of:

urea and derivatives thereof, thiourea and derivatives thereof, phenol and substituted phenols, dihydroxybenzenes and derivatives thereof, hydroquinone and substituted hydroquinones, salicylic acid and derivatives thereof, tri-o-thymotide and derivatives thereof, ascorbic acid, flavins and derivatives thereof, flavanols and derivatives thereof, cyclophane and derivatives thereof, guaiacamine, naphthohydroquinones and derivatives thereof, chromanes and derivatives thereof, including 4-p-hydroxyphenyl-2,2,4-trimethylchroman, 4-p-hydroxyphenyl-2,2,4-trimethylthiochroman, 4-p-hydroxyphenyl-2,2,4,7-tetramethylthiochroman, 4-p-hydroxyphenyl-2,2,4-trimethylseleniumchroman, hexahost compounds, including hexakis(phenylthio) benzene and derivatives thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetrasalicylides, 9,9'-spirobifluorene-2,2'-dicarboxyl acid, choleic acids, 4,4'-dinitrodiphenyl, bis (N,N'-alkylene-benzidine), bis(N,N'-tetramethylenebenzidine), desoxycholic acid, tetra-(4-methylpyridine)nickel(II)-dithiocyanates and derivatives thereof, hexamethylisocyanidoferronchlorides, 2-phenyl-3-p-(2,2,4-trimethylchroman-4-yl)-phenylquinazoline-4, cyclotriphosphazone,and tris-1,2-phenyldioxycyclotriphosphazones, and guest molecules selected from the group consisting of:

inert gases and inert gas compounds, sulfur halides, nitrogen and nitrogen oxides, carbon oxides, hydrogen and hydrogen oxides, sulfur oxides, hydrogen halides and oxygen, as well as hydrocarbons and derivatives thereof, epoxides, ethers and halogenated hydrocarbons wherein the guest is released to form bubbles of the size sufficiently small to pass through the pulmonary capillary bed without the risk of embolism.

6. A method as in claim 5, wherein the ultrasonic contrast agent additionally contains a physiologically compatible vehicle.

7. A method as in claim 5, wherein the amount of the cavitate- or clathrate-forming host/guest complexes of said ultrasonic contrast agent provides a gas volume of at least 150 μl.

8. A method as in claim 5, wherein the guest is released to form bubbles of a size less than 10 μm.

9. Preparation for ultrasonic investigation comprising cavitate- or clathrate-forming host/guest (h/g) complexes whose host molecules are dissolved in the liquid vehicle to release the guest containing host molecules selected from the group consisting of urea and derivatives thereof, thiourea and derivatives thereof, phenol and substituted phenols, dihydroxybenzenes and derivatives thereof, hydroquinone and substituted hydroquinones, salicylic acid and derivatives thereof, tri-o-thymotide and derivatives thereof, ascorbic acid, flavins and derivatives thereof, flavanols and derivatives thereof, cyclophane and derivatives thereof, guaiacamine, naphthohydroquinones and derivatives thereof, chromanes and derivatives thereof, including 4-p-hydroxyphenyl-2,2,4-trimethylchroman, 4-p-hydroxyphenyl-2,2,4-trimethylthiochroman, 4-p-hydroxyphenyl-2,2,4,7-tetramethylthiochroman, 4-p-hydroxyphenyl-2,2,4-trimethylseleniumchroman, hexahost compounds, including hexakis(phenylthio) benzene and derivatives thereof, cyclotriveratrylene and derivatives thereof, 1,1'-binaphthyl-2,2'-dicarboxylic acid and derivatives thereof, onium compounds and derivatives thereof, acetylsalicylic acid, di-, tri- and tetrasalicylides, 9,9'-spirobifluorene-2,2'-dicarboxyl acid, choleic acids, 4,4'-dinitrodiphenyl, bis(N,N'-alkylene-benzidine), bis(N,N'-tetramethylenebenzidine), desoxycholic acid, tetra-(4-methylpyridine)nickel(II)-dithiocyanates and derivatives thereof, hexamethylisocyanidoferronchlorides, 2-phenyl-3-p-(2,2,4-trimethylchroman-4-yl)-phenylquinazoline-4, cyclotriphosphazone, and tris-1,2-phenyldioxycyclotriphosphazones, and guest molecules selected from the group consisting of:

inert gases and inert gas compounds, sulfur halides, nitrogen and nitrogen oxides, carbon oxides, hydrogen and hydrogen oxides, sulfur oxides, hydrogen halides and oxygen, as well as hydrocarbons and derivatives thereof, epoxides, ethers and halogenated hydrocarbons.

10. A preparation for ultrasonic investigation comprising cavitate- or clathrate-forming host/guest (h/g) complexes whose host molecules are dissolved in a liquid vehicle to release the guest, where said host/guest complexes are selected from the group consisting of:

a) urea and derivatives thereof as a host molecule and hydrocarbons as a guest molecule;

b) thiourea and derivatives thereof as a host molecule and a guest molecule selected from the group consisting of hydrocarbons and halogenated hydrocarbons;

c) phenol and substituted phenols as a host molecule and a guest molecule selected from the group consisting of inert gases, hydrocarbons, carbon oxides and sulfur oxides;

d) dihydroxybenzenes and derivatives thereof as a host molecule and a guest molecule selected from the group consisting of inert gases, water, hydrocarbons, carbon oxides, sulfur oxides and hydrogen halides;

e) hydroquinone and substituted hydroquinones as a host molecule and a guest molecule selected from the group consisting of inert gases, sulfur halides, nitrogen, carbon oxides, ethylene oxides and hydrocarbons;

f) tri-o-thymotide and derivatives thereof as a host molecule and a guest molecule selected from the group consisting of hydrocarbons and halogenated hydrocarbons;

g) chromans as a host molecule and a guest molecule selected from the group consisting of inert gases, sulfur halides, nitrogen, ethylene oxide, carbon oxides, sulfur oxides, hydrocarbons and derivatives thereof, ethers and halogenated hydrocarbons;

h) onium compounds and derivatives thereof as a host molecule and a guest molecule selected from the group consisting of water, halogenated hydrocarbons, hydrocarbons and derivatives thereof.

11. A method of performing ultrasonic imaging within an animal or specimen comprising administering to said host or specimen in an amount effective to enhance ultrasonic contrast, cavitate- or clathrate-forming host/guest (h/g) complexes whose host molecules are dissolved in a liquid vehicle to release the guest, said host/guest complexes being selected from the group consisting of:

a) urea and derivatives thereof as a host molecule and hydrocarbons as a guest molecule;

b) thiourea and derivatives thereof as a host molecule and a guest molecule selected from the group consisting of hydrocarbons and halogenated hydrocarbons;

c) phenol and substituted phenols as a host molecule and a guest molecule selected from the group consisting of inert gases, hydrocarbons, carbon oxides and sulfur oxides;

d) dihydroxybenzenes and derivatives thereof as a host molecule and a guest molecule selected from the group consisting of inert gases, water, hydrocarbons, carbon oxides, sulfur oxides and hydrogen halides;

e) hydroquinone and substituted hydroquinones as a host molecule and a guest molecule selected from the group consisting of inert gases, sulfur halides, nitrogen, carbon oxides, ethylene oxides and hydrocarbons;

f) tri-o-thymotide and derivatives thereof as a host molecule and a guest molecule selected from the group consisting of hydrocarbons and halogenated hydrocarbons;

g) chromans as a host molecule and a guest molecule selected from the group consisting of inert gases, sulfur halides, nitrogen, ethylene oxide, carbon oxides, sulfur oxides, hydrocarbons and derivatives thereof, ethers and halogenated hydrocarbons; and h) onium compounds and derivatives thereof as a host molecule and a guest molecule selected from the group consisting of water, halogenated hydrocarbons, hydrocarbons and derivatives thereof.

12. A method of enhancing an ultrasonic image of a patient which comprises administering to a patient an effective amount of an ultrasonic contrast agent comprising cavitate- or clathrate-forming host/guest (h/g) complexes, the host molecules of which dissolve in a liquid vehicle to release the guest, and taking an ultrasonic image of said patient, wherein said host/guest (h/g) complexes are selected from the group consisting of:

a) urea and derivatives thereof as a host molecule and hydrocarbons as a guest molecule;

b) thiourea and derivatives thereof as a host molecule and a guest molecule selected from the group consisting of hydrocarbons and halogenated hydrocarbons;

c) phenol and substituted phenols as a host molecule and a guest molecule selected from the group consisting of inert gases, hydrocarbons, carbon oxides and sulfur oxides;

d) dihydroxybenzenes and derivatives thereof as a host molecule and a guest molecule selected from the group consisting of inert gases, water, hydrocarbons, carbon oxides, sulfur oxides and hydrogen halides;

e) hydroquinone and substituted hydroquinones as a host molecule and a guest molecule selected from the group consisting of inert gases, sulfur halides, nitrogen, carbon oxides, ethylene oxides and hydrocarbons;

f) tri-o-thymotide and derivatives thereof as a host molecule and a guest molecule selected from the group consisting of hydrocarbons and halogenated hydrocarbons;

g) chromans as a host molecule and a guest molecule selected from the group consisting of inert gases, sulfur halides, nitrogen, ethylene oxide, carbon oxides, sulfur oxides, hydrocarbons and derivatives thereof, ethers and halogenated hydrocarbons; and h) onium compounds and derivatives thereof as a host molecule and a guest molecule selected from the group consisting of water, halogenated hydrocarbons, hydrocarbons and derivatives thereof.

13. A method as in claim 12, which enhances the contrast of a cardiac ultrasonic image by injecting an effective amount of said ultrasonic contrast agent into the blood stream of a patient and obtaining an ultrasonic image of the heart.

14. A preparation for ultrasonic investigation comprising cavitate- or clathrate-forming host/guest (h/g) complexes whose host molecules are dissolved in a liquid vehicle to release the guest, said host/guest complexes being selected from the group consisting of:

a) urea and derivatives thereof as a host molecule and hydrocarbons as a guest molecule;

b) thiourea and derivatives thereof as a host molecule and a guest molecule selected from the group consisting of hydrocarbons and halogenated hydrocarbons;

c) hydroquinone and substituted hydroquinones as a host molecule and a guest molecule selected from the group consisting of inert gases, sulfur halides, nitrogen, carbon oxides, ethylene oxides and hydrocarbons;

d) tri-o-thymotide and derivatives thereof as a host molecule and a guest molecule selected from the group consisting of hydrocarbons and halogenated hydrocarbons; and e) chromans as a host molecule and a guest molecule selected from the group consisting of inert gases, sulfur halides, nitrogen, ethylene oxide, carbon oxides, sulfur oxides, hydrocarbons and derivatives thereof, ethers and halogenated hydrocarbons.

15. A preparation for an ultrasonic investigation comprising cavitate or a clathrate forming host/guest (h/g) complexes whose host molecules are dissolved in a liquid vehicle to release the guest, whereas said host is (4-p-hydroxyphenyl-2,2,4-trimethylchroman) and the guest is argon.

* * * * *